(12) United States Patent  (10) Patent No.: US 8,974,426 B2
Corcoran et al.  (45) Date of Patent: Mar. 10, 2015

(54) METHOD OF THERMAL TREATMENT OF A THERMALLY RESPONSIVE MATERIAL OF MEDICAL DEVICES

(75) Inventors: Louise Corcoran, Stuttgart (DE); Lorcan Coffey, Tuebingen (DE); Andrew Jeffrey, Tuebingen (DE); Hartmut Gratwohl, Zimmern (DE); Günter Lorenz, Tübingen (DE)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 1052 days.

(21) Appl. No.: 12/093,588

(22) PCT Filed: Nov. 14, 2006

(86) PCT No.: PCT/EP2006/010904
§ 371 (c)(1),
(2), (4) Date: Dec. 7, 2010

(87) PCT Pub. No.: WO2007/054365
PCT Pub. Date: May 18, 2007

(65) Prior Publication Data
US 2009/0318861 A1   Dec. 24, 2009

Related U.S. Application Data

(60) Provisional application No. 60/736,515, filed on Nov. 14, 2005.

(51) Int. Cl.
*A61M 29/00* (2006.01)
*A61M 25/00* (2006.01)
(Continued)

(52) U.S. Cl.
CPC ........ *B29C 71/0063* (2013.01); *A61M 25/0009* (2013.01); *B29C 71/04* (2013.01); *B29C 35/0261* (2013.01); *B29C 35/0266* (2013.01);
(Continued)

(58) Field of Classification Search
USPC .............................. 604/264, 96.01, 113–114, 604/101.01–101.05, 523
See application file for complete search history.

(56) References Cited

U.S. PATENT DOCUMENTS 4,808,352 A   2/1989  Bhateja
5,499,973 A *  3/1996  Saab .......................... 604/96.01
(Continued)

FOREIGN PATENT DOCUMENTS

DE   2843061   4/1980
EP   0925802   6/1999
(Continued)

OTHER PUBLICATIONS

U.S. Appl. No. 60/736,515, filed Nov. 14, 2005, Jeffrey et al.

*Primary Examiner* — Rebecca E Eisenberg
(74) *Attorney, Agent, or Firm* — Workman Nydegger; Jonathan D. Feuchtwang

(57) ABSTRACT

The present invention relates to a method of thermal treatment of thermally responsive material wherein areas in or on the material to be thermally treated are defined and thermal energy is inputted on or into the defined areas in order to change/influence the material characteristics. The present invention further relates to medical devices or parts thereof manufactured at least in part from thermally responsive material by a process comprising at least one step of thermal treatment of this thermally responsive material.

21 Claims, 4 Drawing Sheets

(51) Int. Cl.
    *B29C 71/00*         (2006.01)
    *B29C 71/04*         (2006.01)
    *B29C 35/02*         (2006.01)
    *B29C 71/02*         (2006.01)
    *B29C 35/08*         (2006.01)
    *B29K 105/24*       (2006.01)
    *B29L 23/00*         (2006.01)
    *B29L 31/00*         (2006.01)

(52) U.S. Cl.
    CPC ........ *B29C 71/02* (2013.01); *B29C 2035/0822* (2013.01); *B29C 2035/0827* (2013.01); *B29C 2035/0838* (2013.01); *B29C 2035/0877* (2013.01); *B29C 2071/022* (2013.01); *B29K 2105/243* (2013.01); *B29K 2995/0082* (2013.01); *B29L 2023/00* (2013.01); *B29L 2023/22* (2013.01); *B29L 2031/753* (2013.01); *B29L 2031/7542* (2013.01)
    USPC ........................................ 604/264; 604/96.01

(56) References Cited

U.S. PATENT DOCUMENTS

| | | | |
|---|---|---|---|
| 5,711,909 | A | 1/1998 | Gore et al. |
| 5,951,495 | A | 9/1999 | Berg et al. |
| 6,214,277 | B1 | 4/2001 | Saigo et al. |
| 6,977,105 | B1 * | 12/2005 | Fujieda et al. ............... 428/36.9 |
| 7,815,975 | B2 * | 10/2010 | Pursley ....................... 427/421.1 |
| 2004/0068249 | A1 * | 4/2004 | Kampa et al. ................. 604/523 |
| 2004/0098110 | A1 | 5/2004 | Williams et al. |
| 2005/0004556 | A1 | 1/2005 | Pursley |
| 2006/0142703 | A1 * | 6/2006 | Carter et al. ................. 604/264 |

FOREIGN PATENT DOCUMENTS

| | | |
|---|---|---|
| EP | 1413422 | 4/2004 |
| WO | WO 2007/054365 | 5/2007 |

* cited by examiner

METHOD OF THERMAL TREATMENT OF A THERMALLY RESPONSIVE MATERIAL OF MEDICAL DEVICES

CROSS REFERENCE TO RELATED APPLICATIONS

This application is a §371 Nationalization of PCT/EP2006/010904 filed Nov. 14, 2006 and which claims priority to U.S. Provisional Patent Application No. 60/736,515, filed Nov. 14, 2005, the disclosures of which are incorporated herein by this reference.

BACKGROUND OF THE INVENTION

1. Field of the Invention

The present invention concerns a method of thermal treatment of a thermally responsive material. Moreover, the invention concerns a method of producing medical devices from thermally responsive material.

2. Background Information

The material of medical devices, e.g. catheters, often has to meet several characteristics like pushability and kink resistance, as well as flexibility and trackability. These characteristics require on one hand a relatively high stiffness in longitudinal direction whilst e.g. a catheter requires a relatively high flexibility at the same time.

In the prior art these needs are addressed by the use of spirals or braidings attached to or incorporated into the polymer materials these devices are made of U.S. Pat. No. 5,951,495 for example describes a tubing having an inner and an outer tube and a wire braid inbetween. U.S. Pat. No. 5,711,909 provides a catheter carrying a helical reinforcement member embedded within the tubular wall of the catheter.

Common drawbacks of the addition of braidings or spirals are the use of multiple components in a tube resulting in larger dimensions, potential delamination as well as complicated and expensive manufacturing processes.

SUMMARY OF THE INVENTION

It is therefore an object of the present invention to provide a new method or process for manufacturing of medical devices or parts of medical devices, which combine desired characteristics like high pushability, kink-resistance, and flexibility. It is further an object of the present invention to provide medical devices or parts of medical devices manufactured by this process.

The solution of this object is achieved by providing a method of thermal treatment of a thermally responsive material in order to be able to influence its material characteristics according to varying prerequisites and/or fields of application. More precisely, the present invention provides a method of thermal treatment of a thermally responsive material being characterized by (a) defining areas in or on the material to be thermally treated; and (b) inputting thermal energy on or into the defined areas in order to change/influence the material characteristics.

The invention is based on the idea to influence the properties of thermally responsive materials, in particular mechanical characteristics and performance such as pushability, kink resistance, flexibility etc. by inputting energy on or into the material in order to re-arrange the morphology and crystallinity in the material structure.

DETAILED DESCRIPTION OF THE PREFERRED EMBODIMENTS

Figure 1:
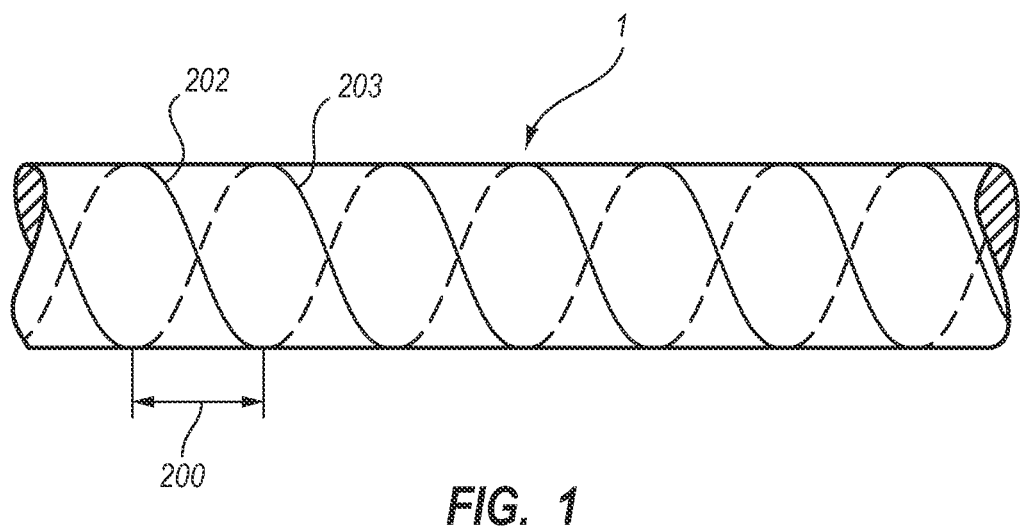
FIG. 1 shows schematically simplified a tube created by the method of the present invention.

The method of the present invention has several embodiments described hereinbelow and partly illustrated in the figures.

The present invention provides a method of thermal treatment of a thermally responsive material being characterized by (a) defining areas in or on the material to be thermally treated; and (b) inputting thermal energy on or into the defined areas in order to change/influence the material characteristics. This process is referred to as thermal transfer annealing (TTA).

The invention is based on the idea to influence the properties of thermally responsive materials, in particular mechanical characteristics and performance as pushability, kink resistance, flexibility etc. by inputting energy on or into the material in order to re-arrange the morphology and crystallinity in the material structure.

According to the principles of the present invention, the molecular structure of the material can be cross-linked in order to enhance its properties and performance for varying fields of application.

Medical devices or parts thereof which can be manufactured according to the present invention include but are not limited to vascular products, closure devices, heart valves, coils, catheters, stents, as well as medical balloons, hollow components, tubes, catheter tips, tip extensions, catheter shafts, catheter tubes.

In a preferred method of producing a medical device comprising thermally responsive material the polymer device or polymer part thereof is manufactured out of the desired polymer to result in its final shape. Subsequently, the manufactured part is subjected to thermal treatment.

In another preferred method of producing a medical device, the semi-finished parts are subjected to thermal treatment. Subsequently, the parts are further processed for manufacturing the device.

Materials suitable for energy treatment according to the present invention include but are not limited to Polyurethanes (PU) (e.g. Tecoflex, Pellethene, Bionate, corethane, Elasteon, and blends thereof); Polyethylenes (PE) (e.g. PET, PBT, PVDF, Teflon, ETFE, and blends thereof); Polyolefins (e.g. HDPE, PE; LDPE; LLDPE, Polypropylene, and blends thereof); Polyimides; Polyamides; all classes of Nylons (e.g. Nylon 11; Nylon 12; Nylon 6,6; Nylon 6; Nylon 7,11; Nylon 11,12, and blends thereof); Blockcopolymers, PEBA-types (e.g. ELY, PEBAX (polyester block amide), Ubesta, and blends thereof); and biodegradable polymers. Also suitable materials are all kinds of blends of the above mentioned materials as well as any composite materials, like duallayers, trilayers and multilayers.

For energy treatment, the individual component consisting of the material to be treated may be placed into an energy source preferably on a mandrel that can for example be coated with PTFE, Polyethylene or polypropylene. The energy source and intensity to be utilized depends on the material to be treated. The term thermal treatment within the scope of this invention includes treatment with various energy sources. The energy sources include but are not limited to wave energy, thermal energy, light energy, laser energy, IR heat, UV light, ultrasound waves and e-beam.

According to the present invention, it is possible to describe any pattern on the outer surface or within the material of the component to be treated, said pattern corresponding to areas that have been defined before the thermal treatment in order to intentionally influence certain regions in or on the material by the thermal treatment. Examples for suitable patterns include but are not limited to spirals with constant or varying pitch, rings, lines, a multiplicity of offset lines, staggered lines, honeycombed patterns as well as any lattice structures, chequered pattern and triangle patterns which taper to the distal portion.

During the treatment the energy that is inputted in the material or onto the material should be controlled such that the energy does not lead to material ablation from the components to be treated but only delivers sufficient energy to encourage especially cross-linking in the material. The temperature range created by the applied energy preferably includes all temperatures above the glass transition temperature ($T_E$) and all temperatures below the melting temperature ($T_M$) of the material to be treated depending on the storage conditions as well as the water content of the material.

The exact pattern, kind and amount of energy and especially a rotational and/or longitudinal speed and pitch of the component to be treated can be selected according to the desired material characteristics to be achieved.

In a preferred embodiment the polymers to be treated according to the present invention are doped with crosslinking agents in order to adjust the degree of crosslinking upon energy treatment. Crosslinking agents which can be employed include but are not limited to α,ω-olefins; 1,7-Octadiene; 1,9-Decadiene; Trivinylcyclohexane (TVCH); TAIC (Trialylisocyanurate) and related compounds; Pyromellitic acid; Benzophenone teracarboxylic dianhydride (BTDA); Pyromellitic dianhydride (PMDA); Trimesic Acid; 5-Hexene-1-ol; Glycidol; 2-Allylphenol; Diallyl bisphenol-A; 1,3-Phenylene-bisoxazoline; Guanamines; and DYHARD.

In another preferred embodiment the polymers to be treated according to the present invention are doped with nucleating agents or clarifying agents in order to make the polymer more prone to the energy treatment and to be able to further adjust the degree of crystallization of the polymer. Nucleating agents or clarifying agents which can be used include but are not limited to sodium benzoate; Sodium 2,2'-Methylene-bis(4,6-di-tert-butylphenyl) phosphate; Sorbitol-derivatives: para-alkyl substituted methyldibenzylidene Sorbitol; Dibenzylidene Sorbitol; Dimethyldibenzlidene Sorbitol; γ-Quinacridon; Pimelic acid/Ca-Stearate; N',N'-Dicyclohexyl-2,6-Naphthaline dicarboxamide; Potassium stearate, Sodium benzoate, micronisiated talcum; $Na_2CO_3$; benzoic acid; CaF; Mg-, Ca-, Zn-salts of adipinic acid; Zn-Phenylphosphinate; Zn-Phenylphosphonate; Na-bis(4-tert-butylphenyl)phosphoric acid; Na/Cl-benzoate; Sodium acids of Pyrrol-carboxylates; Dimethyl-4,4'-terephthaloyldioxidibenzoate; 2-Hydroxybenzimidazole; Bis (phenylbromide) methane; and Aluminium hydroxyl-bis(4-tert-butylbenzoate).

Doping of the polymer can be uniform over the polymer article or restricted to certain areas of the polymer article. Further, the amount of the doping agent can vary over regions of the polymer article. One or more doping agents can be used in combination.

The temperature range of the treatment may include all temperatures above the glass transition temperature ($T_E$) and all temperatures below the melting temperature ($T_M$) for a specific water content of the material to be treated, dependent on storage conditions and water content of the material.

It is a further object of the present invention to provide medical devices or parts thereof manufactured according to the principles of the present invention.

Further advantages and features of the present application will become apparent from the following advantageous embodiments, examples and the description of the drawings.

FIG. 1 shows a part of a medical device according to the present invention. It is shown a cube-like component 1, e.g. of a catheter, featuring two patterns 202 and 203 that have been created by inputting energy into the material and influencing thereby the material characteristics. In the present case, the two patterns 202 and 203 are spirals that are disposed with respect to one another at certain pitches (200) that are shown in the drawing as well.

In another embodiment of the present invention a catheter tip is provided. The catheter tip is manufactured by a process comprising a step of thermal treatment according to the present invention.

Figure 2:
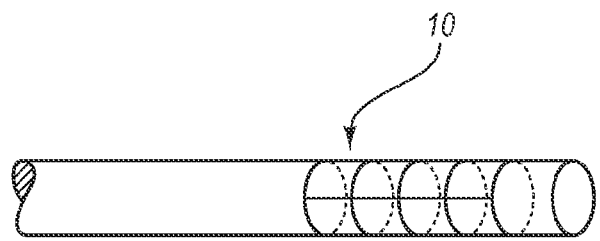
FIGS. 2 to 7 show schematically simplified catheters or catheter parts according to the present invention

In another embodiment as depicted in FIG. 2 the catheter tip (10) is reinforced by a pattern induced in the tip material by thermal transfer annealing. The pattern describes circumferential rings connected by straight lines along the length of the catheter tip. This pattern of reinforced material allows the formation of a catheter tip made from very soft material like e.g. a soft PEBAX (polyester block amide) to provide a very untraumatic, flexible and soft tip, which does not undergo compression and thus still provides good pushability to the catheter. By provision of such catheter tips, high pushability can be achieved also with tips of very small dimensions.

Figure 3:
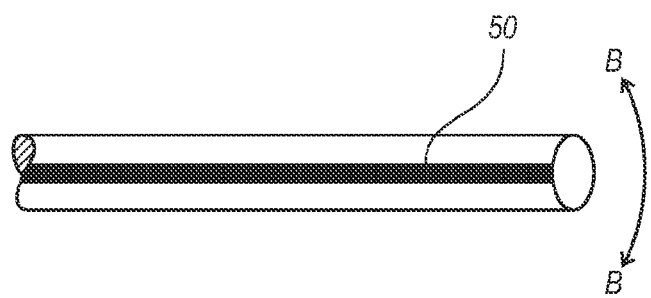

In another example as depicted in FIG. 3, the tip can be made steerable by the provision of a suitable patterns (50) of material reinforced by thermal transfer annealing. FIG. 3 shows a distal portion of a catheter. The catheter tube is reinforced by thermal transfer annealing according to the present invention along the length of the catheter tube on opposite sites. This way, the catheter bends preferably in direction of the region not treated (B) with thermal transfer annealing. This is especially desirable in applications like for example treatment of bifurcations, where the doctor needs to track the catheter into a side branch of the vessel system.

In a further embodiment, catheter shafts are provided according to the present invention which provide high flexibility and trackability to the catheter while still good pushability is assured. The characteristics of the catheter shaft can be easily adjusted by thermal treatment of the tubes or components.

Figure 4:
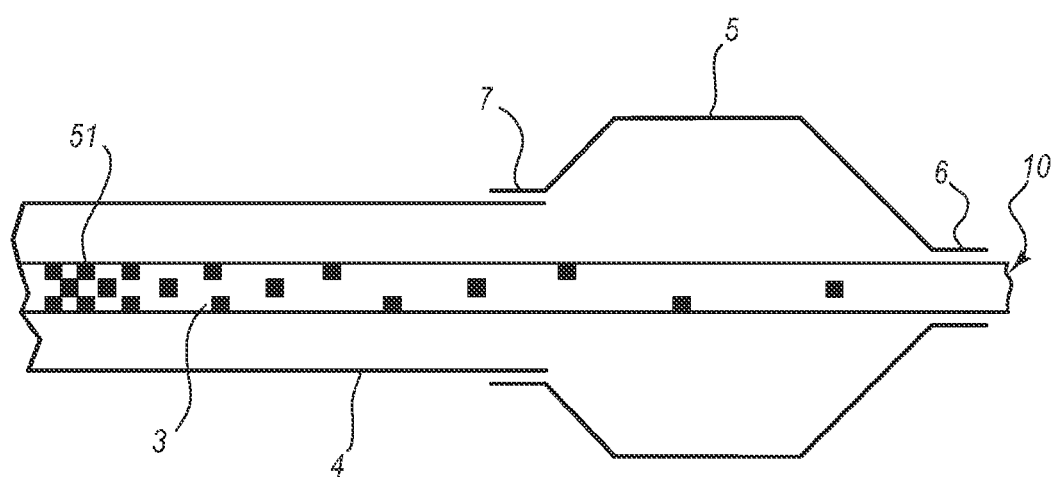

A further embodiment is illustrated in FIG. 4. It is depicted a catheter comprising an inner tube (3), an outer tube (4) and a balloon (5), the distal balloon sleeve (6) mounted to distal region of the inner tube, the proximal balloon sleeve (7) mounted to the distal end of the outer tube. In order to provide varying stiffness of the catheter shaft, the inner tube is partially treated with thermal transfer annealing. In the proximal region the treated and thus reinforced area (51) is bigger than in the distal portion. This way, a transition in stiffness from a relatively stiff proximal end to a relatively flexible distal end id provided. It is obvious to the person skilled in the art, that any pattern with varying density can be applied. It is also obvious that any part of the catheter shaft, inner tube, outer tube or both can be manufactured by a process including a step of the thermal transfer annealing according to the present invention.

Figure 5:
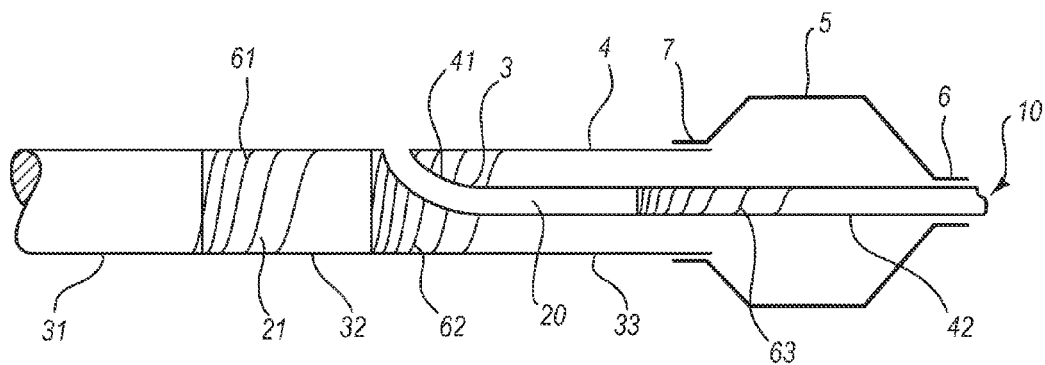

In another embodiment smooth transitions between different catheter tube portions are provided. FIG. 5 shows an RX-catheter comprising an outer tube (4), a guide wire lumen (20), an inflation lumen (21) and a balloon (5), the distal balloon sleeve (6) mounted to distal region of the inner tube, the proximal balloon sleeve (7) mounted to the distal end of the outer tube, whereby the interior of the balloon is in fluid communication with the inflation lumen. The guide wire lumen extends from a region distal of the proximal end of the catheter to a region distal of the distal balloon sleeve. The outer tube comprises at least 3 portions (31, 32, 33) made from different materials in order to provide decreasing stiffness of the catheter in its distal direction. Also the guide wire lumen tube can be assembled from two or more different tube portions (41, 42) with different materials and stiffness. In the transition regions there is always a step in flexibility which is not desired. This step in flexibility can be diminished by the provision of thermally treated regions in the proximal tube portions. In that case, the proximal portion of the tube is reinforced (61, 62, 63), thus its flexibility in the proximal region can be adapted to the flexibility of the distal region of the tube attached proximal to the first tube.

Further, it is a well known problem that RX-catheters tend to kink at the proximal guide wire exit. It is therefore another object of the present invention to provide reinforcement of the region around and especially proximal of the proximal guide wire exit by thermal treatment according to the present invention.

In another embodiment of the present invention, balloons of medical balloon catheters are subjected to thermal treatment.

Figure 6A:
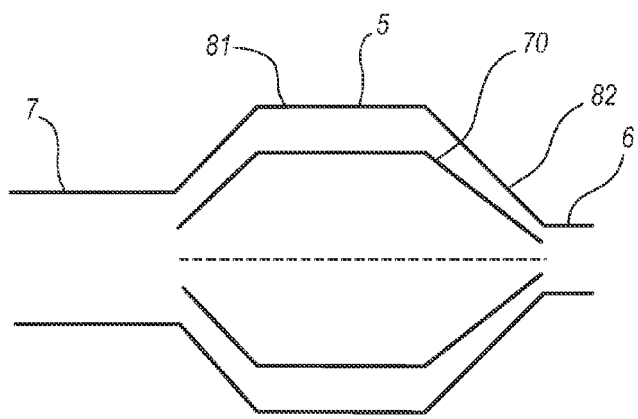
Figure 6B:
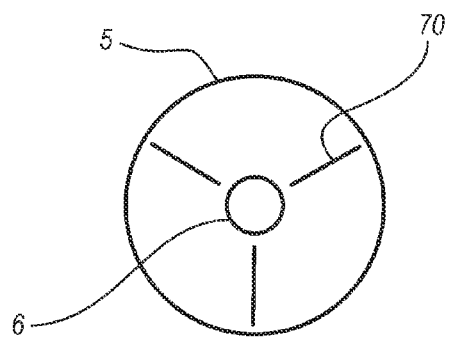

In one preferred embodiment, the balloon is reinforced by thermal treatment along lines along the balloon length. As depicted in FIG. 6A the reinforced lines (70) can extend over the balloon body (81), along the balloon cone (82), or along both. For better visualisation, FIG. 6B shows the balloon in a frontal view. By such a pattern, the rewrapping of the balloon upon balloon deflation can be induced.

Figure 7:
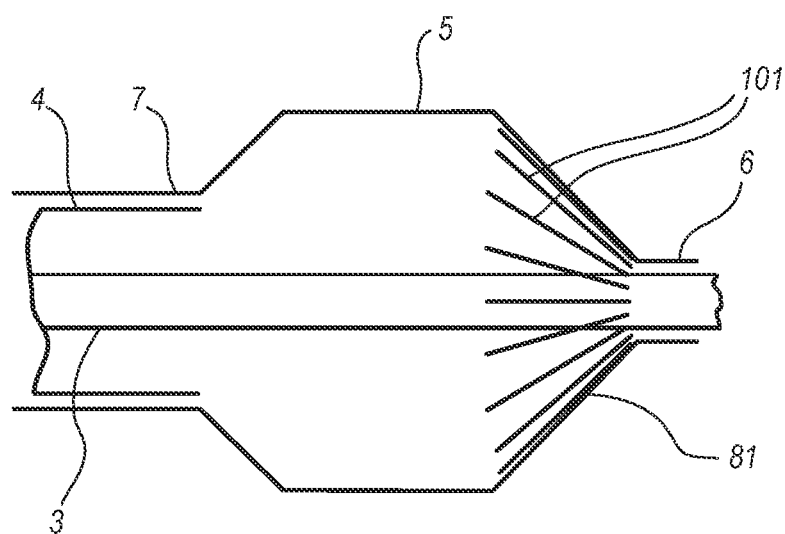

In another embodiment as depicted in FIG. 7 a balloon with thermal transfer reinforced areas (101) in the distal balloon cone (81) is provided to avoid buckling of the balloon when crossing tight lesions or chronic total occlusions.

In an example a tubing according to FIG. 1 was made by employing the process of the present invention. A three layer material tubing consisting of PEBAX (Polyester block amide, Plexar, and HDPE was placed on a Yag laser at 2.5 watt laser settings and then processed under compressed air to create the spiral patterns. The tubing was traversed backwards to create the opposite patterns and complete the spiral shapes.

One skilled in the art would readily appreciate that the present invention is well adapted to carry out the objects and obtain the ends and advantages mentioned, as well as those inherent therein. The methods, processes, and devices described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention claimed is:

1. A catheter comprising a catheter tube having a distal tip with a reinforcement pattern disposed therein, the reinforcement pattern comprising at least one annealed longitudinal pattern along a length of the catheter tube and at least one annealed circumferential ring disposed about the catheter tube, the catheter tube comprising a polymer doped with a doping agent, the doping agent being selected from a crosslinking agent, a nucleating agent or a clarifying agent, wherein the doping agent is distributed uniformly through at least a portion of the polymer such that the doping agent is uniformly distributed through a thickness of the catheter tube, wherein the at least one annealed circumferential ring intersects the at least one annealed longitudinal pattern.

2. A catheter as recited in claim 1, further comprising two annealed longitudinal patterns disposed on opposite sides of the catheter tube.

3. A catheter as recited in claim 1, wherein the distal tip is fabricated from soft Polyester Block Amide.

4. The catheter as recited in claim 1, wherein the catheter includes a proximal guidewire exit and the reinforcement pattern is disposed about the proximal guidewire exit.

5. The catheter in claim 1, wherein the polymer is uniformly doped with a doping agent throughout the polymer.

6. A catheter comprising:
   an inner tube having an annealed area of higher stiffness than the distal portion of the inner tube, the annealed area of higher stiffness comprising at least one annealed longitudinal pattern along a length of the catheter tube and at least one annealed circumferential ring disposed about the catheter tube and the inner tube comprising a polymer doped with a doping agent, the doping agent being selected from a crosslinking agent, a nucleating agent or a clarifying agent, wherein the doping agent is distributed uniformly through at least a portion of the polymer such that the doping agent is uniformly distributed through a thickness of the inner tube;
   an outer tube receiving the inner tube; and
   a balloon having a proximal balloon sleeve and a distal balloon sleeve, the proximal balloon sleeve being coupled to the outer tube and the distal balloon sleeve being coupled to the inner tube.

7. The catheter as recited in claim 6, wherein the annealed area extends towards the distal portion, the stiffness of the annealed area decreasing towards the distal portion.

8. The catheter as recited in claim 6, wherein the outer tube comprises a plurality of tube portions and a plurality of other reinforced areas, the other reinforced areas transitioning stiffness of adjacent tube portions of the plurality of tube portions.

9. The catheter as recited in claim 6, wherein the inner tube comprises a plurality of inner tube portions and a plurality of inner reinforced areas, the inner reinforced areas transitioning stiffness of adjacent inner tube portions of the plurality of inner tube portions.

10. The catheter as recited in claim 6, wherein the balloon comprises at least one reinforced region.

11. The catheter as recited in claim 10, wherein the at least one reinforced region comprises a reinforced line.

12. The catheter as recited in claim 6, wherein the at least one reinforced region comprises a reinforced area.

13. A catheter as recited in claim 6, wherein the inner tube or the outer tube comprises a thermally responsive material.

14. A catheter as recited in claim 13, wherein the reinforced area is annealed through application of wave energy to a temperature above the glass transition temperature ($T_E$) and below the melting temperature ($T_M$) of the thermally responsive material.

15. A catheter comprising:
    an inner tube;
    an outer tube;
    a balloon coupled to the inner tube and the outer tube, the balloon comprising at least one annealed reinforced line extending over at least a portion of a length of the balloon and at least one annealed circumferential ring disposed about the catheter tube, the at least one annealed circumferential ring intersecting the at least one annealed reinforced line, the annealed reinforced line comprising a polymer doped with a doping agent, the doping agent being selected from a crosslinking agent, a nucleating agent or a clarifying agent, wherein the doping agent is distributed uniformly through at least a portion of the polymer such that the doping agent is uniformly distributed through a thickness of the balloon.

16. A catheter as recited in claim 15, wherein the at least one annealed reinforced line extends from a proximal end to a distal end of the balloon.

17. A catheter as recited in claim 15, wherein the balloon is a thermally responsive material.

18. A catheter as recited in claim 15, wherein each of the inner tube and the outer tube comprises a plurality of tube portions.

19. A catheter as recited in claim 15, wherein a proximal end of the inner tube terminates distal to the proximal end of the outer tube.

20. The catheter in claim 15, wherein the annealed reinforce line extends between adjacent circumferential rings.

21. The catheter in claim 15, wherein the catheter tube comprises a Polyester Block Amide layer and a high-density polyethylene layer.

* * * * *